United States Patent
Ekre et al.

(10) Patent No.: US 9,480,702 B2
(45) Date of Patent: *Nov. 1, 2016

(54) USE OF CHEMICALLY MODIFIED HEPARIN DERIVATES IN SICKLE CELL DISEASE

(71) Applicant: DILAFORETTE AB, Solna (SE)

(72) Inventors: Hans-Peter Ekre, Stockholm (SE); Anna Leitgeb, Saltsjöbaden (SE); Mats Wahlgren, Stocksund (SE); Dagmar Pikas, Uppsala (SE)

(73) Assignee: DILAFORETTE AB, Solna (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/366,603

(22) PCT Filed: Dec. 19, 2012

(86) PCT No.: PCT/SE2012/051429
§ 371 (c)(1),
(2) Date: Jun. 18, 2014

(87) PCT Pub. No.: WO2013/095277
PCT Pub. Date: Jun. 27, 2013

(65) Prior Publication Data

US 2014/0364369 A1  Dec. 11, 2014

Related U.S. Application Data

(63) Continuation-in-part of application No. PCT/SE2011/051538, filed on Dec. 19, 2011.

(51) Int. Cl.
*C08B 37/00* (2006.01)
*A61K 31/727* (2006.01)
*A61K 45/06* (2006.01)

(52) U.S. Cl.
CPC .......... *A61K 31/727* (2013.01); *A61K 45/06* (2013.01); *C08B 37/0063* (2013.01); *C08B 37/0075* (2013.01); *C08B 37/0078* (2013.01)

(58) Field of Classification Search
CPC .......... C08B 37/0063; C08B 37/0075; C08B 37/0078; A61K 45/06; A61K 31/727
USPC ............................................. 514/14.9
See application file for complete search history.

(56) References Cited

U.S. PATENT DOCUMENTS

| | | | |
|---|---|---|---|
| 4,303,651 A | 12/1981 | Lindahl et al. | |
| 4,990,502 A | 2/1991 | Lormeau et al. | |
| 5,250,519 A | 10/1993 | Conrad et al. | |
| 5,280,016 A | 1/1994 | Conrad et al. | |
| 5,472,953 A | 12/1995 | Ekre et al. | |
| 5,527,785 A | 6/1996 | Bevilacqua et al. | |
| 5,767,269 A | 6/1998 | Hirsh et al. | |
| 5,993,810 A | 11/1999 | Lebovitz | |
| 6,028,061 A | 2/2000 | Bernfield et al. | |
| 6,486,137 B1 | 11/2002 | Lundqvist et al. | |
| 6,569,840 B1 * | 5/2003 | Yamashina | C08B 37/0075 514/56 |
| 6,596,705 B1 | 7/2003 | Varki et al. | |
| 8,071,569 B2 | 12/2011 | Mousa | |
| 2005/0075314 A1 | 4/2005 | Ekman-Ordeberg et al. | |
| 2005/0215519 A1 | 9/2005 | Viskov et al. | |
| 2006/0040896 A1 * | 2/2006 | Kennedy | A61K 31/727 514/56 |
| 2006/0147415 A1 | 7/2006 | Mousa et al. | |
| 2007/0021378 A1 * | 1/2007 | Varki | A61K 31/727 514/56 |
| 2010/0298263 A1 | 11/2010 | Casu et al. | |
| 2010/0316640 A1 | 12/2010 | Sundaram et al. | |
| 2010/0324276 A1 * | 12/2010 | Sundaram | A61K 31/727 536/21 |
| 2011/0200673 A1 | 8/2011 | Mousa | |

FOREIGN PATENT DOCUMENTS

| | | | | |
|---|---|---|---|---|
| EP | 0735050 B1 | | 9/1902 | |
| EP | 0735050 A2 | * | 10/1996 | ............. C08B 37/10 |
| EP | 0867452 A1 | | 9/1998 | |
| EP | 1059304 A1 | | 12/2000 | |
| EP | 0735050 B1 | * | 10/2002 | ............. C08B 37/00 |
| UA | 21707 | | 3/2007 | |
| WO | 92/02232 A1 | | 2/1992 | |
| WO | 94/08595 A1 | | 4/1994 | |
| WO | 03/055499 A1 | | 7/2003 | |
| WO | 03/088980 A1 | | 10/2003 | |
| WO | 2007014155 A2 | | 2/2007 | |
| WO | 2009007224 A1 | | 1/2009 | |
| WO | 2009059284 A2 | | 5/2009 | |
| WO | 2009/073184 A1 | | 6/2009 | |
| WO | 2009124266 A2 | | 10/2009 | |
| WO | 2010121196 A1 | | 10/2010 | |
| WO | 2011000032 A1 | | 1/2011 | |
| WO | 2013/095276 A1 | | 6/2013 | |
| WO | 2013/095279 A1 | | 6/2013 | |

(Continued)

OTHER PUBLICATIONS

Bazin et al., "Inhibition of Apolipoprotein E-Related Neurotoxicity by Glycosaminoglycans and Their Oligosaccharides," Biochemistry 41(25):8203-8211 (2002).
Garg et al., "Heparin Oligosaccharide Sequence and Size Essential for Inhibition of Pulmonary Artery Smooth Muscle Cell Proliferation," Carbohydrate Research 337(21-23)2359-2364 (2002).
Guerinni et al., "Antithrombin-binding Octasaccharides and Role of Extensions of the Active Pentasaccharide Sequence in the Specificity and Strength of Interaction: Evidence for Very High Affinity Induced by an Unusual Glucuronic Acid Residue," J. of Biol. Chem 283(39):26662-26675 (2008).
Leitgeib et al., "Low Anticoagulant Heparin Disrupts Plasmodium falciparum Rosettes in Fresh Clinical Isolates," Am J. Trop. Med. Hyg. 84(3):390-396 (2011).
Suda et al. "Structural Characterization of Heparin's Binding Domain for Human Platelets," Thrombosis Research 69(6):501-508 (1993).

(Continued)

*Primary Examiner* — Ganapathy Krishnan
(74) *Attorney, Agent, or Firm* — LeClairRyan, a Professional Corporation

(57) ABSTRACT

The present invention relates to chemically modified heparin for use in the treatment of sickle cell disease, with an antifactor II activity of less than 10 IU/mg, an antifactor Xa activity of less than 10 IU/mg and an average molecular weight (Mw) between about 6.5 and 9.5 kDa.

12 Claims, 10 Drawing Sheets

(56) References Cited

FOREIGN PATENT DOCUMENTS

| WO | 2013/147689 A1 | 10/2013 |
|---|---|---|
| WO | 2013/147690 A1 | 10/2013 |

OTHER PUBLICATIONS

International Search Report for PCT/SE2011/051538 (mailed Sep. 3, 2012).
International Search Report and Written Opinion for PCT/SE2012/051429 (mailed May 21, 2013).
Combs et al., "Factors Associated With Hemorrhage in Cesarean Deliveries," Obstetrics and Gynecology, 77(1):77-82 (1991).
Henry et al., "Perinatal Outcomes in the Setting of Active Phase Arrest of Labor," Obstetrics and Gynecology, 112 (5):1109-1115 (2008).
Isma et al., "The Effect of Low Molecular Weight Heparin (Dalteparin) on Duration and Initiation of Labour," J Thromb Thrombolysis 30:149-153 (2010).
The Merck Manual of Diagnosis and Therapy, 17th Ed., Beers and Berkow, Eds., Ch. 253. "Abnormalities and Complications of Labor and Delivery,"; Ch. 254: "Postpartum Care"; pp. 2062-2067 (1999).
Van Lennep et al., "Prophylaxis with Low-Dose Low-Molecular-Weight Heparin During Pregnancy and Postpartum: Is It Effective?," Journal of Thrombosis and Haemostasis, 9:473-480 (2011).
Yousuf and Haider, "Postpartum Hemorrhage: An Experience At Tertiary Care Hospital," Journal of Surgery Pakistan (International), 14(2):80-84 (2009).
Rudd et al., "High-Sensitivity Visualization of Contaminants in Heparin Samples by Spectral Filtering of $^1$H NMR Spectra," Analyst 136:1390-1398 (2011).
Wei et al., "High-Dose vs Low-Dose Oxytocin for Labor Augmentation: A Systematic Review," Am. J. Obstetrics & Gynecology 203(4): 296-304 (2010).
Alfirevic et al.,"Prevention of Post-Partum Hemorrhage with Misoprostol," Int. J. Gynecology Obstetrics 99:S198-S201 (2007).
Dildy, "Postpartum Hemorrhage: New Management Options," Clinc. Obstetrics & Gynecology 45(2):330-344 (2002).
Kadanali et al., "Comparison of Labor Induction with Misoprostol vs. Oxytocin/Prostaglandin E2 in Term Pregnancy," International Journal of Gynecology & Obstetrics 55:99-104 (1996).
Belayet et al., "Binding of Interleukin-8 to Heparan Sulphate Enhances Cervical Maturation in Rabbits," Molecular Human Reproduction 5(3):261-269 (1999).
Vogt et al., "Release of Sequestered Malaria Parasites Upon Injection of a Glycosaminoglycan," PLOS Path. 2(9):0853-0863 (2006).
Dondorp et al., "Levamisole Inhibits Sequestration of Infected Red Blood Cells in Patients with Falciparum Malaria," J. Infect. Dis. 196:460-466 (2007).
Silamut et al., "A Quantitative Analysis of the Microvascular Sequestration of Malaria Parasites in the Human Brain," Am. J. Pathol. 155(2):395-410 (1999).
Dilafor press release: Potential Treatment for Severe Malaria completes Phase I Study (Oct. 13, 2009).
Dilafor press release: Dilafor Announces the Selected INN for DF02, Sevuparin (Aug. 30, 2010).
Dilafor press release: Dilaforette Initiates a Phase I/II Study with Sevuparin for the Treatment of Severe Malaria (Sep. 23, 2011).
Who Drug Information, 25(4):437-438 (2011).
Who Drug Information, 26(3):323 (2012).
Lindahl et al., "Evidence for a 3-O-Sulfated D-Glucosamine Residue in the Antithrombin-Binding Sequence of Heparin," Proc. Nat. Acad. Sci. U.S.A. 77(11):6551-6555 (1980).
Casu et al., "Undersulfated and Glycol-Split Heparins Endowed with Antiangiogenic Activity," J. Med. Chem. 47:838-848 (2004).
Naggi et al., "Glycol-Splitting as a Device for Modulating Inhibition of Growth Factors and Heparanase by Heparin and Heparin Derivatives," Chemistry and Biology of Heparin and Heparin Sulfate, Elsevier, Amsterdam pp. 461-481 (2005).

Naggi et al., "Modulation of the Heparanase-Inhibiting Activity of Heparin through Selective Desulfation, Graded N-Acetylation, and Glycol Splitting," J. Biol. Chem. 280(13):12103-12113 (2005).
Alekseeva et al., "Profiling Glycol-Split Heparins by HPLC/MS Analysis of their Heparinase-Generated Oligosaccharides," Anal. Biochem. 434(1):112-122 (2013).
Alekseeva et al., "Structural Features of Glycol-Split Low-Molecular-Weight Heparins and their Heparin Lyase Generated Fragments," Anal. Bioanal. Chem. 406:249-265 (2014).
Clinicaltrials.gov: A Phase I/II, Randomized, Open Label, Active Control, Parallel Assignment, Safety/Efficacy Study of Sevuparin/DF02 as an Adjunctive Therapy in Subjects Affected with Uncomplicated Falciparum Malaria (May 7, 2015).
Carlson et al., "Disruption of Plasmodium Falciparum Erythrocyte Rosettes by Standard heparin and Heparin Devoid of Anticoagulant Activity," Am. J. Trop. Med. Hyg. 46(5):595-602 (1992).
von der Lehr, "Battle Against Clever Parasite," Kemisk Tidskrift Nr 7-8:24-26 (2011).
Kulane et al., "Effect of Different Fractions of Heparin on Plasmodium Falciparum Merozoite Invasion of Red Blood Cells in Vitro," Am. J. Trop. Med. Hyg. 46(5):589-594 (1992).
Ware et al., "Advances in the Use of Hydroxyurea," Am. Soc. Hematol. pp. 62-69 (2009).
Chaplin et al., "Preliminary Trial of Minidose Heparin Prophylaxis for Painful Sickle Cell Crises," E. African Med. J. 66(9):574-584 (1989).
Qari et al., "Reduction of Painful Vaso-Occlusive Crisis of Sickle Cell Anaemia by Tinzaparin in a Double-Blind Randomized Trial," Thromb. Heamost. 98:392-396 (2007).
Blumenkrantz et al., "New Method for Quantitative Determination of Uronic Acids," Analytical Biochem. 54:484-489 (1973).
Bachelet et al., "Affinity of Low Molecular Weight Fucoidan for P-Selectin Triggers its Binding to Activated human Platelets," Biochimica Biophysica Acta 1790:141-146 (2009).
Zennadi et al., "Epinephrine Acts Through Erythroid Signaling Pathways to Activate Sickle Cell Adhesion to Endothelium via LW-{alpha}v{beta}3 Interactions," Blood 104:3774-3781 (2004).
Zennadi et al., "Epinephrine-Induced Activation of LW-Mediated Sickle Cell Adhesion and Vaso-Occlusion in Vivo," Blood 110:2708-2717 (2007).
Batchvarova et al., "Sevuparin Reduces Adhesion of Both Sickle Red Cells and Leukocytes to Endothelial Cells in Vitro and Inhibits Vaso-Occlusion in Vivo," Abstract #58733, New Orleans (Dec. 7-10, 2013) (ASH).
Brodszki et al., "A Novel Treatment Approach for Paediatric Gorham-Stout Syndrome with Chylothorax," Acta Paediatrica 100:1448-1453 (2011).
Fransson et al., "Structural Studies on Heparan Sulphates. Characterization of Oligosaccharides; Obtained by Periodate Oxidation and Alkaline Elimination," Eur. J. Biochem. 106:59-69 (1980).
Guerrini et al., "Complex Glycosaminoglycans: Profiling Substitution Patterns by Two-Dimensional Nuclear Magnetic Resonance Spectroscopy," Analytical Biochem 337:35-47 (2005).
Shaker et al., "Uterine Contractions Due to Heparin," British Med. J. pp. 408-409 (1974).
Osmers et al., "Glycosaminoglycans in Cervical Connective Tissue During Pregnancy and Parturition," Obst. Gynecol. 81(1):88-92 (1993).
Blanks et al., "Myometrial Function in Prematurity," Best Pract. Res. Clin. Obst. Gynaecol. 21(5):807-819 (2007).
Fransson et al., "Relationship Between Anticoagulant Activity of Heparin and Susceptibility to Periodate Oxidation," FEBS Lett. 97(1):119-123 (1979).
Su, "Postpartum Hemorrhage," Prim. Care Clin. Office Pract. 39:167-187 (2012).
Belghiti et al., "Oxytocin During Labour and Risk of Severe Postpartum Haemorrhage: A Population-Based, Cohort-Nested Case-Control Study," BMJ Open 1(e000514):1-9 (2011).
Ekman-Ordeberg et al., "Low Molecular Weight Heparin Stimulates Myometrial Contractility and Cervical Remodeling in Vitro," Acta Obstetricia et Gynecologica 88:984-989 (2009).

(56) References Cited

OTHER PUBLICATIONS

Hjelm Cluff et al., "Prolonged Labour Associated with Lower Expression of Syndecan 3 and Connexin 43 in Human Uterine Tissue," Reproduc. Biol. Endocrinol. 4:24 (2006).
Akerud, "Uterine Remodeling During Pregnancy. Studies on the Effect of Heparin/Heparan Sulfate," Department of Experimental Medical Science (2009).
International Nonproprietary Names for Pharmaceutical Substances: List 64, p. 24.
Who Drug Information 23(4) Proposed International Nonproprietary Names for Pharmaceutical Substances: List 102 (2009).
Karolinska Development Press Release—Portfolio Company Completes Successful Phase II Clinical Trial (Sep. 4, 2009).
Invitation to Subscribe for Shares in Karolinska Development p. 45 (Mar. 25, 2011) p. 46 (Apr. 14, 2011).
Clinicaltrials.gov: A Randomized, Double-Blind, Placebo-Controlled, Multicenter Trial to Assess the Safety and Efficacy or Pre-Treatment with DF01 During Late Pregnancy in Reducing Prolonged Labor (May 19, 2015).
Roos et al., "Prostaglandin Receptors in the Human Cervix at Term and Post Term Pregnancy—Genetic Expression and Localization," Poster S-071 Reproduct. Sci. 18(4):Supplement (Mar. 2011).
Ekman-Ordeberg et al., "Tafoxiparin a New Drug Counteracting Labor Arrest by Increased Myometiral Contractility and Enhanced Cervical Cytokine Synthesis," Poster Presentation at Birth Labor Congress (Chicago, 2011) and Society of Gynecologic Investigations (Miami, 2010).
Dilafor press release: Promising Results from Phase II Trial Show New Treatment from Dilafor Prevents Protracted Labor in Childbirth (Sep. 3, 2009).
Barragan et al., "The Duffy-Binding-Like Domain 1 of Plasmodium falciparum Erythrocyte membrane Protein 1 (PfEMP1) is a Heparan Sulfate Ligand that Requires 12 Mers for Binding," Blood 95(11):3594-3599 (2000).
Ekman-Ordeberg et al., "Does Low Molecular Weight Heparin Shorten Term Labor?" Acta Obstetricia et Gynecologica 89:147-150 (2010).
Lau et al., "Inhibitors of Slit Protein Interactions with the Heparan Sulphate Proteoglycan Glypican-1: Potential Agents for the Treatment of Spinal Cord Injury," Clin. Exper. Pharmacol. Physiol. 37:417-421 (2010).
Skidmore et al., "Disruption of Rosetting in Plasmodium falciparum Malaria with Chemically Modified Heparin and Low Molecular Weight Derivatives Possessing Reduced Anticoagulant and Other Serine Protease Inhibition Activities," J. Med. Chem. 51:1453-1458 (2008).
Wiesner et al., "New Antimalarial Drugs," Angew. Chem. Int. Ed. 42:5274-5293 (2003).

\* cited by examiner

GlcN - UA - GlcN - UA - GlcN - UA - GlcN

R= –H or –SO$_3^-$

R´= COCH$_3$ or –SO$_3^-$

R= COCH$_3$ or –SO$_3^-$

USE OF CHEMICALLY MODIFIED HEPARIN DERIVATES IN SICKLE CELL DISEASE

This application is a national stage application under 35 U.S.C. §371 of PCT Patent Application No. PCT/SE2012/051429, filed Dec. 19, 2012, which claims the priority benefit of PCT Patent Application No. PCT/SE2011/051538, filed Dec. 19, 2011.

TECHNICAL FIELD

The present invention relates to novel chemically modified heparins with low anticoagulant activity, their use in therapy, such as sickle cell disease.

BACKGROUND OF THE INVENTION

Heparin is a naturally occurring glycosaminoglycans (GAGs) that is synthesized by and stored intracellulary in so-called mast cells in humans and animals. Prepared industrially from porcine intestinal mucosa, heparin is a potent anticoagulant and has been used clinically for more than 60 years as the drug of preference for prophylaxis and treatment of thromboembolic disorders. The major potential adverse effects of heparin treatment are bleeding complications caused by its anticoagulant properties. Heparin is highly polydisperse and composed of a heterogeneous population of polysaccharides with molecular weights ranging from 5 to 40 kDa, with the average being approximately 15 to 18 kDa Low molecular weight/mass heparins (LMWH) according to European pharmacopeia 6.0 are defined as "salts of sulfated GAGs having a mass-average molecular mass less than 8 and for which at least 60 percent of the total mass has a molecular mass less than 8 kDa." "Low molecular mass heparins display different chemical structures at the reducing or the non-reducing end of the polysaccharide chains." "The potency is not less than 70 IU of anti-factor Xa activity per milligram calculated with reference to the dried substance. The ratio of anti-factor Xa activity to anti-factor IIa activity is not less than 1.5." Clinically used LMWHs have molecular weights ranging from 3 to 15 kDa with an average of approximately 4 to 7 kDa. Produced by controlled depolymerization/fractionation of heparin, LMWHs exhibits more favorable pharmacological and pharmacokinetic properties, including a lower tendency to induce hemorrhage, increased bioavailability and a prolonged half-life following subcutaneous injection. Heparin exerts its anticoagulant activity primarily through high-affinity binding to and activation of the serine proteinase inhibitor, antithrombin (AT). Binding is mediated by a specific pentasaccharide sequence. AT, an important physiological inhibitor of blood coagulation, neutralizes activated coagulation factors by forming a stable complex with these factors. Binding of heparin causes a conformational change in AT that dramatically enhances the rate of inhibition of coagulation factors, thereby attenuating blood coagulation and the formation of blood clots.

Sickle cell disease (SCD) is an inherited disorder due to homozygosity for the abnormal hemoglobin, hemoglobin S (HbS). This abnormal HbS is caused by the substitution of a single base in the gene encoding the human (3-globin subunit. Its reach is worldwide, but predominantly affects people suffering from malaria, primarily in equatorial Africa, but also in the Mediterranean-, India, and Middle East. The vaso-occlusive phenomena and hemolysis are clinical hallmarks of SCD. Vaso-occlusion results in recurrent painful episodes (sometimes called sickle-cell crisis) and a variety of serious organ system complications such as secondary infections, acute chest syndrome, stroke, and splenic sequestration. Vaso-occlusion accounts for 90% of hospitalizations in children with SCD, and it can ultimately lead to life-long disabilities and/or early death. On a molecular level, P-selectin is one of several targets that have been shown to be an important receptor in mediating the adhesion of blood cells to the vessel wall as part of the events leading to vaso-occlusion.

The presently dominating therapy of managing SCD includes the use of hydroxyurea (Ware et al American Society of Hematology, 2009, pp 62-65). However, this treatment has only limited efficacy and includes a number of side-effects for the patients. Chaplin et al (see East Afr Med J. 1989; 66(9):574-84) performed a pilot trial with daily prophylactic dose of heparin in four patients with sickle cell crises and successfully demonstrated pain reduction and fewer days at hospital. Qari et al. (Thromb. Haemost, 2007, 98, 392-6) describe a clinical study where a low molecular weight heparin derivative, tinzaparin, was used, reporting beneficial effects of the treatment, but also several cases of bleeding events.

WO 03/088980 suggests an oral treatment with heparin or heparin subfractions for the treatment of vaso-occlusion (VOC) in SCD.

DESCRIPTION OF THE INVENTION

The present invention relates to chemically modified heparin for use in the treatment of sickle cell disease. In the context of the present invention, anti-coagulant activity of heparin relates to the clinical function of potentiating inhibition of coagulation factors Xa and IIa (thrombin) by AT. Other terms will be defined in relevant contexts in the following description.

In one aspect, the invention is directed to chemically modified heparin for use in the treatment of sickle cell disease, having an antifactor II activity of less than 10 IU/mg, an antifactor Xa activity of up to 10 IU/mg and an average molecular weight from about 6.5 to about 9.5 kDa, wherein the polysaccharide chains:
(i) comprise from 2 to 25 disaccharide units corresponding to molecular weights from 1.2 to 15 kDa;
(ii) have a reduction in chemically intact saccharide sequences providing an antithrombin-mediated anticoagulant effect, when compared to the polysaccharide chains of native heparin and have a reduction in unsulfated iduronic and/or glucuronic acid units when compared to native heparin.

In one aspect of the invention a chemically modified heparin for use in the treatment of sickle cell disease has from 2 to 25 disaccharide units corresponding to molecular weights from about 1.2 to about 15 kDa. Chemically modified heparins have polysaccharide chains with a reduction in chemically intact pentasaccharide sequences responsible for the anti-thrombin (AT) mediated anticoagulant effect, when compared to the chains of native heparin and have polysaccharide chains with a reduction in unsulfated iduronic and glucuronic acid residues when compared to native heparin.

Chemically modified heparins for use in the treatment of sickle cell disease have predominantly occurring polysaccharide chains with between 6 and 16 disaccharide units with molecular weights between 3.6 and 9.6 kDa. The term "predominantly" does in this context have the meaning of "the frequently most present" polysaccharide chains.

An aspect of the invention is that a chemically modified heparin has at least 30% of the polysaccharide chains with a molecular weight of at least 8 kDa.

An aspect of the invention is that a chemically modified heparin comprises chains terminated by a threonate residue or by a derivative of threonate, such as esters or amides thereof. The threonate residue is depicted below as a terminal group.

In an aspect of the invention is that, from 3 to 15% of the polysaccharide chains of the chemically modified heparin have a molecular mass of at least 15 kDa.

In an aspect of the invention, from 25 to 47% of the polysaccharide chains of the chemically modified heparin have a molecular mass of at least 9 kDa.

In an aspect of the invention, from 40 to 60% of the polysaccharide chains of the chemically modified heparin have a molecular mass of at least 7 kDa.

In an aspect of the invention, from 60 to 80% of the polysaccharide chains of the chemically modified heparin have a molecular mass of at least 5 kDa.

In an aspect of the invention, 85% of the polysaccharide chains of the chemically modified heparin have a molecular mass of at least 3 kDa.

In an aspect of the invention, 95% of the polysaccharide chains of the chemically modified heparin have a molecular mass of at least 2 kDa.

In yet an aspect, the chemically modified heparins of the invention for use in the treatment of sickle cell disease have a distribution of polysaccharides and their corresponding molecular mass expressed as cumulative % of weight according the table:

| Molecular mass, kDa | Cumulative weight, % |
|---|---|
| >15 | 3-15 |
| >9 | 25-47 |
| >7 | 40-60 |
| >5 | 60-80 |
| >3 | >85 |
| >2 | >95 |

In yet an aspect, the chemically modified heparins of the invention for use in the treatment of sickle cell disease have a distribution of polysaccharides and their corresponding molecular mass expressed as cumulative % of weight according the table:

| Molecular mass, kDa | Cumulative weight, % |
|---|---|
| >15 | 3-15 |
| >10 | 18-38 |
| >9 | 25-47 |
| >8 | 30-55 |
| >7 | 40-60 |
| >6 | 50-72 |
| >5 | 60-80 |
| >4 | 72-86 |
| >3 | >85 |
| >2 | >95 |

Chemically modified heparins according for use in the treatment of sickle cell disease have polysaccharide chains with the disaccharide depicted below as the predominant structure with a terminal threonate residue. The predominant disaccharide has a molecular weight of about 600 Da.

(n is an integer of 2-25).

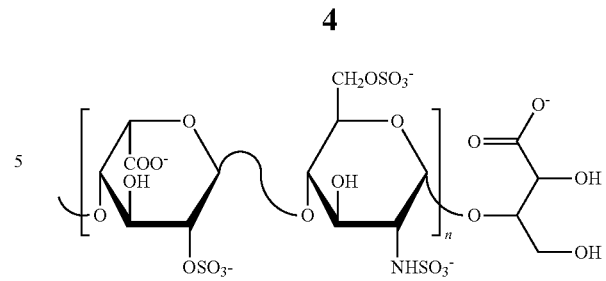

According to yet an aspect of the invention, chemically modified heparins for use in the treatment of sickle cell disease comprise glycol-split residues with the chemical structure:

Glycol-split residues appear in polysaccharide chains of chemically modified heparins, as a result of the oxidation and reduction processes, as earlier discussed in the context with the method and the specific hydrolysis step. They can also be regarded as indicative of the efficacy of the earlier described depolymerization (hydrolysis) step. It is further referred to U.S. Pat. No. 4,990,502 for a chemical reference of the appearance of glycol-split residues. The depicted glycol spilt residue arrives from oxidation and reduction of unsulfated iduronic acid and glucuronic acid.

An aspect of the invention is a chemically modified heparin for use in the treatment of sickle cell disease has a $^1$H-NMR spectrum in the range of from 5.0 to 6.5 ppm that complies with a $^1$H-NMR spectrum from native heparin by the absence of any proton signals with a magnitude above 0.1 (mol) %.

In one aspect of the invention, chemically modified heparins for use in the treatment of sickle cell disease described are expected to comply with presently accepted heparin standards by having an $^1$H-NMR spectrum meeting the heparin acceptance criterion set out by EDQM, Council of Europe, 2012, for example by not having any unidentified signals larger than 4 percent compared to the height of the heparin signal at 5.42 ppm in the ranges 0.10-2.00 ppm, 2.10-3.10 ppm and 5.70-8.00 ppm.

In one aspect of the invention chemically modified heparin for use in the treatment of sickle cell disease has polysaccharide chains which retain at least 90% of the sulfate groups of a corresponding native heparin. In other terms chemically modified heparins according to the invention have a loss of sulfate groups of about one sulfate group per disaccharide unit of 100 disaccharide units, corresponding to a loss of sulfate groups of less than 1% of the total sulfate content, when assuming that heparin contains in average 2.4 sulfate groups per disaccharide unit and that there is one sulfate group per iduronic acid, I2S and 2 sulfate groups for the predominant glucosamine variant, GlcNS.

In one aspect of the invention, chemically modified heparin for use in the treatment of sickle cell disease may be useful for therapies previously disclosed as associated with other regions of heparin than the binding site to AT. Examples include, but are not limited, to such areas as treatment of inflammation, treatment of neurodegenerative diseases, tissue repair, stroke, prevention and treatment of shock, especially septic shock and prevention of the development of metastases.

An aspect of the invention is a chemically modified heparin for use in the treatment of painful crises in sickle cell disease (vaso-occlusive crisis). Chemically modified heparins as herein disclosed, may be useful in the prevention or treatment of occlusive effects from sickle-blood cells, caused by abnormal adhesive effects in the blood. Chemically modified heparins according to the invention have a binding affinity to P-selectin comparable to that of heparin.

An aspect of the invention is a chemically modified heparin as herein disclosed, as an add-on therapy to pain management and therapy with hydroxyurea.

In still an aspect of the invention, a chemically modified heparin as herein disclosed may be administered simultaneously, or sequentially, in the meaning of an adjunct treatment with a medicament effective against sickle cell disease or complications from sickle cell disease.

Yet an aspect of the invention, is a method for the treatment of sickle cell disease, comprising the administration to patient in need of such treatment, a therapeutically effective amount of a chemically modified heparin as herein described. In one aspect the method comprises treatment of vaso-occlusive crisis.

Yet an aspect of the invention is a pharmaceutical composition comprising a chemically modified heparin as herein described, together with a pharmaceutically and pharmacologically acceptable carrier. In yet an aspect of the invention, a pharmaceutical composition as herein described, may be administered systemically by parenteral administration, such as by subcutaneous or intravenous injection. In yet an aspect, a pharmaceutical composition as herein described, may be administered orally. For parenteral administration, the active compounds can be incorporated into a solution or suspension, which also contain one or more adjuvants such as sterile diluents such as water for injection, saline, fixed oils, polyethylene glycol, glycerol, propylene glycol or other synthetic solvents, antibacterial agents, antioxidants, chelating agents, buffers and agents for adjusting the osmolality. The parenteral preparation can be delivered in ampoules, vials, prefilled or disposable syringes also for self administration, or as infusion arrangements, such as for intravenous or subcutaneous infusion. Chemically modified heparins according to the invention may be administered subcutaneously and with suitable self-administration tools, such as injectors.

Pharmaceutical compositions comprising a chemically modified heparin as herein described, can comprise combinations of one or several conventional pharmaceutically acceptable carriers. The carriers or excipients can be solid, semisolid or liquid material that can serve as a vehicle for the active substance. The compositions can be administered in a single dose every 24 h for a period of 1-30, preferably 1-10 days. The dose may be between 0.5-6 mg/kg bodyweight given, either intravenously every 6 or 8 hours, or 1-4 times daily given subcutaneously. An estimated single dose is 25-100 mg/d of modified GAGs, but may be up to 1 g or more. The dose is related to the form of administration. The described pharmaceutical compositions can further comprise additional agents suitable for treating sickle cell disease with supplementary or complementary therapies as outlined in the previous section.

A specific therapeutic use of the chemically modified heparins according to the present invention is treatment of SCD. The chemically modified heparins of the invention will prevent or treat occlusive effects from SCD caused by abnormal adhesive effects in the blood. Also in the treatment of SCD, a therapy including the inventive heparins can be combined with other therapies suitable for treating SCD, either administered simultaneously or administered adjunct to the chemically modified heparins. The complementary therapies preferably alleviate SCD or its secondary complications by other ways of mechanism than the chemically modified heparins and may include administration of agents conventionally used for treating SCD.

The invention further extends to any method of treating SCD or use to producing agents for treating SCD with the described chemically modified heparins.

In summary, the invention generally derives from the understanding that a modified heparin would need to retain a sufficient amount of the sulfate groups included in the native form, in order to exert a therapeutic activity unrelated to anticoagulant effects, for example selectin inhibition as well as other heparin-dependent biological effects.

DETAILED AND EXEMPLIFYING DESCRIPTION OF THE INVENTION

One aspect of the invention is a chemically modified heparin for use in the treatment of sickle cell disease having the International proprietary name (INN) sevuparin sodium, also known as DF02. These terms are used interchangeable and shall have same meaning.

DESCRIPTION OF THE DRAWINGS

FIG. 2 shows the structure of the penta-saccharide unit in heparin required for its binding to AT.

EXAMPLE 1

Figure 1:
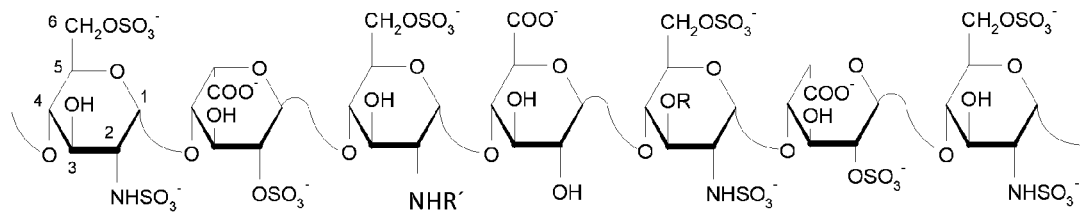
FIG. 1 shows a representative example of heparin sequence
Figure 2:
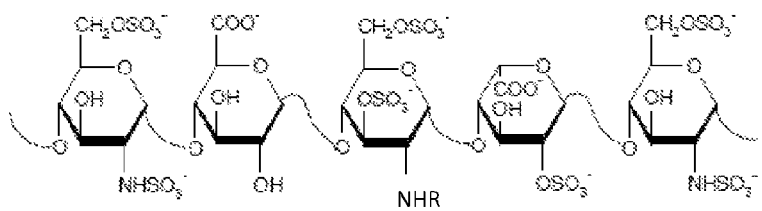

Both heparin and LMWH are composed of repeating disaccharide units containing one uronic acid residue (D-glucuronic or L-iduronic acid, UA) and one D-glucosamine moiety (GlcN) that is either N-sulfated or N-acetylated. These carbohydrate residues may be further O-sulfated, at the C-6 and C-3 positions in the case of glucosamine and the C-2 position of the UA. The structure of heparin is variable regarding distribution of UA and sulfate residues; a representative partial sequence is shown in FIG. 1 (which also illustrates the mode of numbering of carbon atoms in a monosaccharide residue). FIG. 2 shows the unique, pentasaccharide sequence distributed within heparin polymers which is essential for the binding to AT. Several structural characteristics of this sequence have been shown to be crucial for the interaction of heparin with AT. Notably, one of the two UA residues present in this pentasaccharide sequence is consistently sulfated at the C-2 position; whereas the hydroxyl groups at both C-2 and C-3 of the other uronic moiety are unsubstituted.

Figure 3:
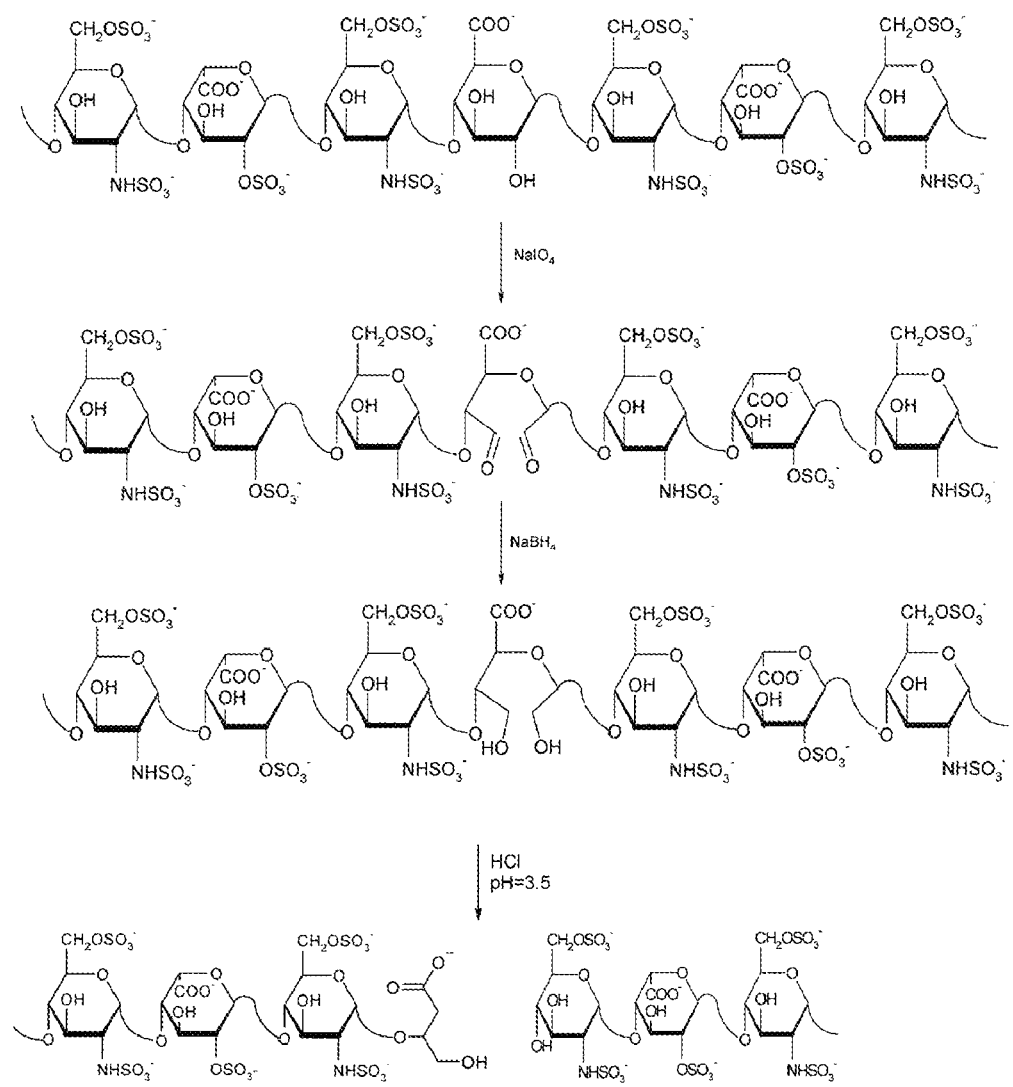
FIG. 3 shows a scheme of the synthesis of the chemically modified heparin DF02 according to the invention.
Figure 4:
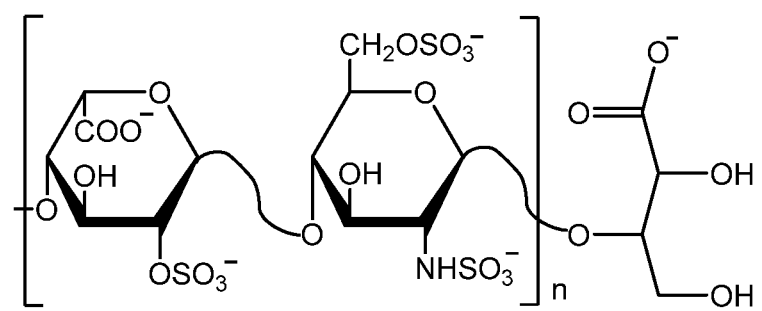
FIG. 4 shows the predominant structure of DF02.

Detailed Description of the Manufacturing Process of Chemically Modified Heparins According to the Invention FIG. 3 schematically shows the manufacturing of a chemically modified heparin according to the present invention, hereinafter designated DF02, while the following sections outline the manufacturing steps.

The substance is prepared from Heparin Sodium. The preparation involves selective oxidation of non-sulfated ironic acid residues in heparin by period ate, including the glucuronic acid moiety in the pentasaccharide sequence that binds AT. Disruption of the structure of this residue annihilates the high-affinity interaction with AT and, consequently, the anticoagulant effect (measured as a-FXa or a-FIIa, see Table 4 and 5). Subsequent reduction and treatment by acid results in cleavage of the polymer at the sites that has been oxidized by periodate. Together, these manipulations lead to a loss of anticoagulant activity along with adequate depolymerization of the heparin chain.

Subsequently, additives, impurities and side-products are removed by repeated precipitations with ethanol, filtration and centrifugations. Thereafter the substance is obtained in powder form by drying with vacuum and heat. The drug substance DF02 is dissolved in a sterile aqueous buffer to yield the drug product, which is intended for intravenous or subcutaneous administration.

Oxidation of Glucuronic and Iduronic Acid (Residues), Deletion of Anticoagulant Activity A quantity of about 3000 grams of Heparin is dissolved in purified water to obtain a 10-20% w/v solution. The pH of this solution is adjusted to 4.5-5.5. The sodium metaperiodate ($NaIO_4$) is subsequently added to the process solution; quantity of periodate is 15-25% of the weight of heparin. The pH is again adjusted to 4.5-5.5. The reactor is covered in order to protect the reaction from light. The process solution is reacted during 22-26 hours with constant stirring and maintenance of the temperature at 13-17° C. The pH at the end of the reaction period is measured and recorded.

Termination of the Oxidation Reaction and Removal of Iodine-Containing Compounds Ethanol (95-99.5%) is added to the reaction mixture over a period of 0.5-1 hour, with careful stirring and at a temperature of 20-25° C. The volume of ethanol to be added is in the range 1-2 volumes of ethanol per volume of process solution. The oxidized heparin is then allowed to precipitate and sediment for 15-20 hours, after which the mother liquor is decanted and discarded.

Next, the sediment is dissolved in purified water to obtain a 15-30% w/v process solution. Then NaCl is added to obtain a concentration of 0.15-0.30 mol/liter in the process solution. Stirring continues for another 0.5-1 hour while maintaining the temperature of 20-25° C. Subsequently 1.0-2.0 volumes of ethanol (95-99.5%) per volume of process solution are added to this solution with careful stirring, during a period of 0.5-1 hour. This precipitates the product from the solution. This precipitation continues for >1 hour.

Reduction of Oxidized Glucuronic/Iduronic Acids

After the mother liquor has been decanted and discarded, the sediment is dissolved by addition of purified water until a concentration of the process solution of 15-30% w/v is obtained. While maintaining the temperature at 13-17° C., the pH of the solution is adjusted to 5.5-6.5. A quantity of 130-150 grams of sodium borohydride is then added to the solution and dissolved, the pH will immediately increase to a pH of 10-11, and the reaction is continued for 14-20 hours. The pH of the solution, both prior to and after this reaction period, is recorded. After this reaction time, a dilute acid is added slowly in order to adjust the pH to a value of 4, this degrades remaining sodium borohydride. After maintaining a pH of 4 for 45-60 minutes, the pH of the solution is adjusted to 7 with a dilute NaOH solution.

Acid Hydrolysis to Achieve Depolymerization of the Polysaccharide Chains

A dilute acid is added to the solution until a pH of 3.5 (acceptable range 3.2-3.8) is obtained.

The temperature is kept at 50-55° C. while stirring the solution for 3 hours+/−10 minutes. A dilute NaOH solution is then added until a pH of 7.0 is obtained and the reaction solution is cooled down to a temperature of 13-17° C. Sodium chloride (NaCl) is then added until a concentration of 0.2-0.3 mol/liter is obtained.

Purification of the Product

Removal of Process Additives and Impurities, Addition of Counter-Ions and Filtration One volume of process solution is then added to 1.5-2.5 volumes of ethanol (95-99.5%) followed by centrifugation at >2000 G, and at <20° C. for 20-30 minutes, after which the supernatant is decanted and discarded.

The resulting product paste obtained by centrifugation is then dissolved in purified water to obtain a product concentration of 10-20% w/v. Then NaCl is added to obtain a concentration of 0.20-0.35 mol/liter. Further, 1.5-2.5 volumes of ethanol (95-99.5%) are added per volume of process solution which precipitates the product from the solution. Centrifugation follows at >2000 G, and at <20° C. for 20-30 minutes after which the supernatant is decanted and discarded.

Next the remaining paste is added to purified water to dissolve. The product concentration would now be in the range of 10-20% w/v. The pH of the product solution is adjusted to 6.5-7.5. The solution is then filtered to remove any particulates. Then, 1.5-2.5 volumes of ethanol (95-99.5%) is added to one volume of process solution. Centrifugation follows at >2000 G, and at <20° C. for 20-30 minutes after which the supernatant is decanted and discarded.

Reduction of the Size and Water Content of the Precipitate Paste

A glass reactor is then filled with ethanol, volume 2 liter. While stirring the ethanol, the precipitate paste is added. The mechanical stirring solidifies the paste and replaces the water present by the ethanol giving a homogenous particle suspension. The stirring is discontinued after 1-2 hours after which the particles are allowed to sediment, then the mother liquor is decanted. This procedure is repeated twice. The precipitate is isolated on a polypropylene (PP) filter. This procedure was repeated two more times. After removal of excessive liquid, the particles are passed through a sieve to obtain smaller and uniform sized particles.

Vacuum Drying

The product is distributed evenly onto two pre-weighed trays, and placed in a vacuum cabinet. The pressure is reduced with a vacuum pump, the pressure actually obtained being noted, and the trays are heated to 35-40° C., with constant recording of the temperature. A stream of nitrogen is passed through the drier at this time while maintaining the low pressure in the dryer. When a constant weight is obtained, i.e. no further evaporation is noticed, the drying is considered complete. The dry product is dispensed, packed and protected from moisture. Storage is performed in a dry area at a temperature of 20-25° C.

The so manufactured product can be prepared as drug product by a conventional aseptic process, such as a solution comprising 150 mg/mL of chemically modified heparin active agent and Na phosphate to 15 mM, pH 6-8. The so obtained drug product is intended for intravenous or subcutaneous administration. The resulting chemically modified heparin, DF02, is a depolymerized form of heparin with a projected average molecular weight of 6.5-9.5 kDa and with essentially no anticoagulant activity.

DF02 has a size distribution of polysaccharide polymers, with a range for n of 2-25 corresponding to molecular weights of 1.2-15 kDa. The predominant size is 6-16 disaccharide units corresponding to molecular weights of 3.6-9.6 kDa.

By practical tests it can be found that reaction of the oxidized heparin preparation in alkaline solution gives rise to chains that are too short, or lack the proper degree of sulfatation, for the optimal pharmaceutical function of the resulting heparin. Further by practical tests, it can be shown that treatment of the heparin preparation in a solution of less than pH 1, leads to desulfatation of the product, and thus giving rise to a chemically modified heparin with less than optimal pharmacologic effect.

TABLE 1

Distribution of polysaccharides and their corresponding molecular mass in DF02 (several batches) as cumulative % of weight

| Molecular mass, kDa | Cumulative weight, % |
| --- | --- |
| >15 | 3-15 |
| >10 | 18-38 |
| >9 | 25-47 |
| >8 | 30-55 |
| >7 | 40-60 |
| >6 | 50-72 |
| >5 | 60-80 |
| >4 | 72-86 |
| >3 | >85 |
| >2 | >95 |

The corresponding value for weight average molecular weight, Mw falls in the range 6.5-9.5 kDa

TABLE 2

Distribution of polysaccharides and their corresponding molecular mass in DF02 as cumulative % of weight for an individual batch

| Molecular mass, kDa | Cumulative weight, % |
| --- | --- |
| >15 | 6.4 |
| >10 | 22.6 |
| >9 | 28.8 |
| >8 | 36.3 |
| >7 | 45.2 |
| >6 | 55.3 |
| >5 | 66.2 |
| >4 | 77.1 |
| >3 | 87.2 |
| >2 | 95.6 |

The corresponding value for molecular weight average weight, Mw is 7.4 kDa

EXAMPLE 2

Example 2 represents a modified version of the manufacturing process according to Example 1. Certain process parameters have been modified, such as process temperatures, with the purpose of preventing any non-specific depolymerization in the initial part of the process
Oxidation of Glucuronic and Iduronic Acid (Residues), Deletion of Anticoagulant Activity A quantity of about 3000 grams of Heparin is dissolved in purified water to obtain a 10-20% w/v solution. The pH of this solution is adjusted to 4.5-5.5. The sodium metaperiodate ($NaIO_4$) is subsequently added to the process solution; quantity of periodate 15-25% of the weight of heparin. The pH is again adjusted to 4.5-5.5. The reactor is covered in order to protect the reaction from light. The process solution is reacted during the 22-26 hours with constant stirring and maintenance of the temperature at 13-17° C., while the temperature is lowered to about 5° C. during the last two hours. The pH at the end of the reaction period is measured and recorded.
Termination of the Oxidation Reaction and Removal of Iodine-Containing Compounds Ethanol (95-99.5%) is added to the reaction mixture over a period of 0.5-1 hour, with careful stirring and at a temperature of about 5° C. The volume of ethanol to be added is in the range 1-2 volumes of ethanol per volume of process solution. The oxidized heparin is then allowed to precipitate and sediment for 15-20 hours, after which the mother liquor is decanted and discarded.

Next, the sediment is dissolved in purified water to obtain a 15-30% w/v process solution. Then NaCl is added to obtain a concentration of 0.15-0.30 mol/liter in the process solution. Stirring continues for another 0.5-1 hour while maintaining a temperature of about 5° C. Subsequently 1.0-2.0 volumes of ethanol (95-99.5%) per volume of process solution.
is added to this solution with careful stirring, during a period of 0.5-1 hour. This precipitates the product from the solution. This precipitation continues for >1 hour.
Reduction of Oxidized Glucuronic/Iduronic Acids This step is made in accordance with Example 1.
Acid Hydrolysis to Achieve Depolymerization of the Polysaccharide Chains This step is performed in accordance with Example 1 with the difference that the process time may be extended about two hours before pH is raised to 7.0 with NaOH.

The further process steps towards a drug product comprising for example 150 mg/ml chemically modified heparin active agent is identical to the steps outline in Example 1.

By performing the process steps according to Example 2, a chemically modified heparin with a polysaccharide molecular weight distribution demonstrated in Table 1 of Example 1 is obtained

EXAMPLE 3

Example 3 represents another method to manufacture chemically modified heparins according to the invention modified by directly subjecting the process solution arriving from the oxidation step to a strong reducing agent, before any precipitation step is introduced.
Oxidation of Glucuronic and Iduronic Acid (Residues), Deletion of Anticoagulant Activity A quantity of about 3000 grams of Heparin is dissolved in purified water to obtain a 10-20% w/v solution. The pH of this solution is adjusted to 4.5-5.5. The sodium metaperiodate (NaIO$_4$) is subsequently added to the process solution; quantity of periodate 15-25% of the weight of heparin. The pH is again adjusted to 4.5-5.5. The reactor is covered in order to protect the reaction from light. The process solution is reacted during the 22-26 hours with constant stirring and maintenance of the temperature at 13-17° C. The pH at the end of the reaction period is measured and recorded.

Reduction of Oxidized Glucuronic/Iduronic Acids and Elimination of Oxidizing Iodine Containing Compounds While maintaining the temperature at 13-17° C., the pH of the solution is adjusted to 5.5-6.5. A quantity of 130-180 grams of sodium borohydride is then added to the solution and dissolved, the pH will immediately increase to a pH of 10-11, and the reaction is continued for 14-20 hours. The pH of the solution, both prior to and after this reaction period, is recorded. After this reaction time, a dilute acid is added slowly in order to adjust the pH to a value of 4, this degrades/neutralizes remaining sodium borohydride. After maintaining a pH of 4 for 45-60 minutes, the pH of the solution is adjusted to 7 with a dilute NaOH solution.

Removal of Iodine-Containing Compounds

Ethanol (95-99.5%) is added to the reaction mixture over a period of 0.5-1 hour, with careful stirring and at a temperature of 20-25° C. The volume of ethanol to be added is in the range 1-2 volumes of ethanol per volume of process solution. The oxidized and subsequently reduced heparin is then allowed to precipitate and sediment for 15-20 hours, after which the mother liquor is decanted and discarded.

Next, the sediment is dissolved in purified water to obtain a 15-30% w/v process solution. Then NaCl is added to obtain a concentration of 0.15-0.30 mol/liter in the process solution. Stirring continues for another 0.5-1 hour while maintaining the temperature of 15-25° C. Subsequently 1.0-2.0 volumes of ethanol (95-99.5%) per volume of process solution is added to this solution with careful stirring, during a period of 0.5-1 hour. This precipitates the product from the solution. This precipitation continues for >1 hour.

Acid Hydrolysis to Achieve Depolymerization of the Polysaccharide Chains

After the mother liquor has been decanted and discarded, the sediment is dissolved by addition of purified water until a concentration of the process solution of 15-30% w/v is obtained.

A dilute acid is added to the solution until a pH of 3.0 is obtained. The temperature is kept at 50-55° C. while stirring the solution for 5 to 10 hours. The progress of depolymerization may be followed by in-process analyses of the molecular weight, by GPC-HPLC as to determine the actual time of reaction required. A dilute NaOH solution is then added until a pH of 7.0 is obtained and the reaction solution is cooled down to a temperature of 13-17° C. Sodium chloride NaCl is then added until a concentration of 0.2-0.3 mol/liter is obtained. Alternatively, in order to similarly control the average molecular weight, the dilute acid can be added to obtain a pH of 3.5, but to accomplish a comparable level of hydrolysis the process time is extended from 5 to hours to 8 to 9 hours, both alternatives yields, an average molecular weight which is kept within the specification range of 6.5 and 9.5 kDa.

The remaining process steps towards a drug product comprising for example 150 mg/ml chemically modified heparin active agent is identical to the steps outlined in Example 1.

By performing the process steps according to Example 3, a chemically modified heparin with a polysaccharide molecular weight distribution demonstrated in Table 1 of Example 1 is obtained.

TABLE 3

Intensity of signals present in $^1$H-NMR spectra compared to heparin in the range of 5 to 6.5 ppm

| Batch produced according to: | Intensity of signals % | | | |
|---|---|---|---|---|
| | 6.14 ppm | 6.00 ppm | 5.94 ppm | 5.90 ppm |
| Example 1 | 1.0 | 1.0 | 6.0 | 1.0 |
| Example 2 | 5.1 | 1.7 | 0 | 2.3 |
| Example 3 batch 1 | 0 | 0 | 0 | 0 |
| Example 3 batch 2 | 0 | 0 | 0 | 0 |
| Example 3 batch 3 | 0 | 0 | 0 | 0 |
| Heparin | 0 | 0 | 0 | 0 |

Table 3 is a result of comparing studies of $^1$H-NMR spectra in the range of 5.0 to 6.5 pp, of chemically modified heparins produced according to Examples 1 to 3.

Table 3 confirms that a chemically modified heparin as manufactured with the process according to Example 3 results in a $^1$H-NMR spectrum with absence of unexpected signals in the range 5.90 ppm to 6.14 ppm equivalent to that of heparin. These signals show a correlation to partially unsaturated, double bond structures containing glucose amines, which may undergo further chemical modifications and contribute to discoloration of the product. In other terms, the process according to Example 3, does not result in unidentified residues or structures that are unexpected in the proton spectra from conventional heparins or low-molecular weight heparin.

In order to confirm that methods according to the invention contribute to retain a desired level of sulfated polysaccharide chains, tests was performed with a sulfate measuring electrode on samples of process liquid from the step of acidic hydrolysis, i.e. samples from process liquid not subjected to the directly subsequent steps of work-up and purification to a chemically modified heparin product. The results demonstrate levels of released (lost) sulfate from polysaccharides generally below 1500 ppm. In other terms the tests confirm that the inventive methods induce a loss of sulfate groups not exceeding one sulfate group per saccharide unit of 100 saccharide units. Chemically modified heparins according to the invention contain one sulfate group per iduronic acid, I2S and 2 sulfate groups for the predominant glucosamine variant, GlcNS. Accordingly, the chemically modified heparins according to the invention retain at least 90% sulfate groups corresponding to heparin.

Chemically modified heparin produced in accordance with processes of Example 3 and worked up to a product exhibit a very low absorbance at 400 nm (10% solution). Absorbance values vary between 0.02 AU and 0.04 AU for a product when subjected to the process including the hydrolysis at pH 3.5 or 3.0 respectively. The low absorbance values confirm that effects from any non-specific depolymerization associated with discoloration from side reactions of Maillard type (measured as absorbance at 400 nm) are minimized and that suitable stability of the chemically modified heparin products according to the invention are expected.

EXAMPLE 4

Antihaemostatic and Anticoagulation Effects

Studies of effects on coagulation parameters and on bleeding after treatment with DF02 were performed in male, adult and juvenile, Sprague-Dawley rats. Heparin and a LMWH preparation (Fragmin) were also studied for comparison. Test procedures were as follows:

Fifteen minutes after i.v. dosing of test article the rats had a longitudinal incision made at the dorsal mid-section of the tail. The incision was 9 mm long and 1 mm deep and was standardized using a template device. Blood was blotted from the incision until bleeding stopped. The time during which visible bleeding could be observed was measured, for up to 25 minutes. The longer the bleeding time, the more pronounced the anti-coagulant effects of the administered agent.

Adult Rat

Forty minutes after dosing, the rats were sacrificed by terminal bleed. Citrate stabilized plasma was prepared from the blood. Plasma was stored in aliquots of 1 or 0.5 mL at −70° C. until analysis of APTT and PT.

The following compounds and doses were tested (each in groups of 8 rats) in adult rats:
Saline: (Negative Control)
Heparin: 0.7, 1.5, 3.5, and 7.0 mg/kg
Fragmin: 1.5, 3.5, 7.0 and 35 mg/kg
DF02: 3.5, 7.0, 35, 70, 105, 210, 350 and 700 mg/kg Juvenile Rat The following compounds and doses were tested (each in groups of 8 rats) in juvenile rats of age 14±1 days:
2. Saline: (Negative Control)
3. DF02: 7.0, 35, 70 and 105 mg/kg Bleeding time and coagulation parameters as measured in adult animals revealed that DF02 has a reduced anti-coagulant effect in rats (See Table below). The potency of DF02 was less than that of the anticoagulants Heparin and Fragmin, which both had profound dose-related effects on all parameters investigated. However, the effect of DF02 on PT was too weak to allow for comparative estimates to the other treatments.

Established bleeding time and coagulation parameters in juvenile animals, indicate that DF02 has a reduced anticoagulant effect also in juvenile rats. The change in bleeding time and coagulation parameters in the juvenile rats are of the same magnitude as in adult rats. As in the adult, the effect of DF02 on PT was weak also in the juvenile rats.

Estimated equipotent doses with respect to effects on bleeding time and APTT, normalized vs. heparin, are demonstrated in Table 3, below.

TABLE 3

|  | DF02 | Heparin | Fragmin |
| --- | --- | --- | --- |
| Bleeding time | 30-50 | 1 | 5 |
| APTT | 30-40 | 1 | 5 |

Table 4 and 5 below show data to demonstrate the inherent activity of DF02 on the anticoagulation parameters in drug substance and drug product, respectively. The drug product is the formulation of DF02 in 150 mg/ml in phosphate buffer; for clinical use.

The Measured values on the produced DF02 on antiIIa and antiXa activity show that the activity is less than 10 IU/mg.

TABLE 4

|  | DF02 | Heparin | Fragmin |
| --- | --- | --- | --- |
| Bleeding time | 30-50 | 1 | 5 |
| APTT | 30-40 | 1 | 5 |

Table 5 below show the specific anticoagulant activities of DF02 by anti-factor Xa and anti-factor IIa assays.

TABLE 5

| Drug substance | | Batch Results | | |
| --- | --- | --- | --- | --- |
| Property | Procedure | Batch 1 | Batch 2 | Batch 3 |
| Anti-coagulant FIIa activity | Ph. Eur. (chromogenic assay) | 4.6 IU/mg | 5.0 IU/mg | 3.8 IU/mg |
| Anticoagulant activity anti-factor Xa | Ph. Eur. | 3.9 IU/mg | 4.9 IU/mg | 5.5 IU/mg |

For comparison, the corresponding value for Unfractionated Heparin (UFH) is at least 180 IU/mg.

EXAMPLE 5

Binding of DF02 to P-Selectin, Analyzed by Optical Biosensor

The aim of this study was to investigate the binding properties of DF02, made according to Example 1, to human P-selectin. The binding properties of DF02 were compared to those of the LMWH tinzaparin and of UFH. Tinzaparin was specifically chosen for this comparison, as a double-blind randomized-controlled study of tinzaparin in sickle VOC (Quart et al 2007) showed that it significantly shortened duration of hospitalization as well as duration of the most-severe pain scores.

Method

Low anticoagulant heparin DF02 batch 342, was manufactured under GMP status while Heparin Sodium salt (batch 1035-0753, pharmaceutical quality) and Tinzaparin natrium (Innohep®, 10,000 anti-Xa IE/ml.) was purchased. The heparin derivatives were desalted and transferred into running buffer using desalting columns. The molar concentrations of the eluates were determined by analysis of UA content (mg/ml) using the phenylphenol method (Blumenkrantz et al. 1973 Anal Biochem 54, 484-9). For DF02, the average molecular weight (Mw) was determined by National Institute for Biological Standards and Control, UK, using gel permeation chromatography (GPC-HPLC, Ph. Eur.) to be 7.4 kDa (Mn=4.1 kDa, Mp=3.4 kDa). Mw for tinzaparin was determined and found to be Mw=6.4 kDa (Mn=5.1 kDa, Mp=6.5 kDa). A commonly used molecular weight number for heparin is 15 kDa although not possible to determine by the GPC-HPLC method. This number was used to calculate the approximate molar concentration of UFH. Real-time biomolecular interactions were analyzed by surface plasmon resonance technology using a Biacore 2000 instrument and Biacore 2000 control software version 3.1.1. The data was analyzed using BIAevaluation software, version 3. To prepare the biosensor assay, the capturing affinity purified goat anti-human IgG Fc antibody was immobilized onto a carboxymethyl dextran chip. The antibody was injected at a concentration of 50 µg/ml in 50 mM sodium acetate buffer, pH 5.0 for 12 min at 20 resulting in a final response of approximately 16,200 response units (RU) in flow cell 1 and 13,400 RU in flow cell 2. Remaining activated groups were blocked with an injection of ethanolamine-HCl. The P-selectin/Fc chimera was captured onto the antibody surface in flow cell 2 (Bachelet L. et al. 2009, Biochim et Biophys Acta 1790, 1416), by injecting the molecule at a concentration of 35 ug/ml, using running buffer (10 mM Hepes, 150 mM NaCl, 1 mM CaCl2, 0.005% Tween-20, pH 7.4, filtered 0.02 µm) in the mobile phase. Typically, this resulted in a response of about 2000 RU. The binding of different heparin derivatives to P-selectin was analyzed using running buffer at 20 µl/min. After the association and dissociation phase of each sample, regeneration of the surface was performed using running buffer containing 0.8 M NaCl. Data from the reference surface was subtracted from the data from the P-selectin surface. Stability of the P-selectin surface was verified by measuring the response from injections of 0.1 mg/mL heparin in the beginning and the end of each experiment.

Results

The response data at steady-state was plotted against the concentration (data not shown). The data was analyzed using non-linear regression, assuming 1:1 binding. This assumption gives apparent KD values of 0.7 µM for DF02, 4 µM for tinzaparin and 0.2 µM for heparin. The peak value (Mp) was used instead of the (higher) Mw value when calculating the molar concentrations of UFH. This results in an overestimation of the molar concentrations used in the experiment as well as an overestimation of the KD value for UFH.

In conclusion, DF02, as well as UFH and the LMWH tinzaparin, binds to human P-selectin in vitro. The apparent KD values were in the order tinzaparin>DF02>UFH. The data suggests that higher average molecular weight of the heparin derivative results in higher apparent affinity (or avidity) to the P-selectin surface, and that the binding is not dependent on the anticoagulant activity of heparin.

EXAMPLE 6

In Vitro Sickle-Red Blood Cell Adhesion

In order to determine the therapeutic efficacy in SCD, in vitro studies of the ability of DF02 to inhibit adhesion of sickle red cells (SS RBC) to endothelial cells were studied. The activity of DF02 was compared to inhibitory P-selectin monoclonal antibodies as well as the LMWH tinzaparin. Tinzaparin was specifically chosen as a double-blind randomized-controlled study of tinzaparin in sickle VOC showed that it significantly shortened duration of hospitalization as well as duration of the most-severe pain.

Method

Primary HUVECs (passage 4 only) were cultured to confluency on gelatin-coated slides in Eagle basal medium 2 (EBM2; Clonetics, Walkersville, Md.) supplemented with endothelial growth medium 2 (EGM2; Clonetics, Walkersville, Md.). For each assay, a gelatin coated slide with HUVECs grown to confluence was mounted inside a graduated height flow chamber. Both untreated and IL-13/histamine-stimulated slides were initially studied with each SS RBC sample. Subsequent experiments then compared adhesion with and without potential inhibitors of adhesion. In addition, tinzaparin was used for comparison of the anti-adhesive activity of DF02 and blocking and non-blocking antibodies to P-selectin were used as controls for confirming SS RBC adhesion to P-selectin.

Human blood samples from patients homozygous for hemoglobin S were collected into citrate tubes. SS RBCs were separated from the buffy coat by gravity at 4° C. for at least 2 hours, and SS RBCs were then washed 4 times in sterile PBS with 1.26 mM Ca2+ and 0.9 mM Mg2+ (pH 7.4). Packed SS RBCs were fluorescently labeled for adhesion studies as previously described (Zennadi et al 2004).

Test System: Flow Chamber Methodology

In vitro studies of cell adhesion exposed to flowing conditions represent in vivo events, as compared to adhesion assays in which cells are simply allowed to incubate overlaid on a chemical or cellular substrate (e.g. laminin or endothelial cells) and then washed off by either non-controlled forces (e.g. pipette washes) or controlled forces (e.g. rotary motion devices). Flow chambers can produce either a constant shear stress throughout the chamber or a variable shear stress, produced by creating a variable height for the chamber.

Confirmation of Expression of P-Selectin by Endothelial Cells after Stimulation with IL-13 and Histamine, Using Indirect Immunofluorescence and Flow Cytometric Analysis.

Surface expression of P-selectin on IL-13 and histamine stimulated and unstimulated endothelial cells (HUVECs) were tested by flow cytometry. Measurement of the ability of SS RBC to adhere to these endothelial cells was performed in flow chambers. Negative control experiments included untreated endothelial cells, so that SS RBC adhesion to treated and untreated cells could be compared. In general, at least 5 patient SS RBC samples were tested in each set of conditions, using different dilutions of DF02, with control experiments as described above.

Stimulation of Expression of P-Selectin by Human Umbilical Vein Endothelial Cells Multiple dose-finding experiments were conducted. Dependence of SS RBC adhesion on P-selectin was also demonstrated by using the monoclonal anti P-selectin antibody 9E1 to inhibit SS RBC adhesion to IL-13+histamine-stimulated HUVECs.

Results

Figure 5:
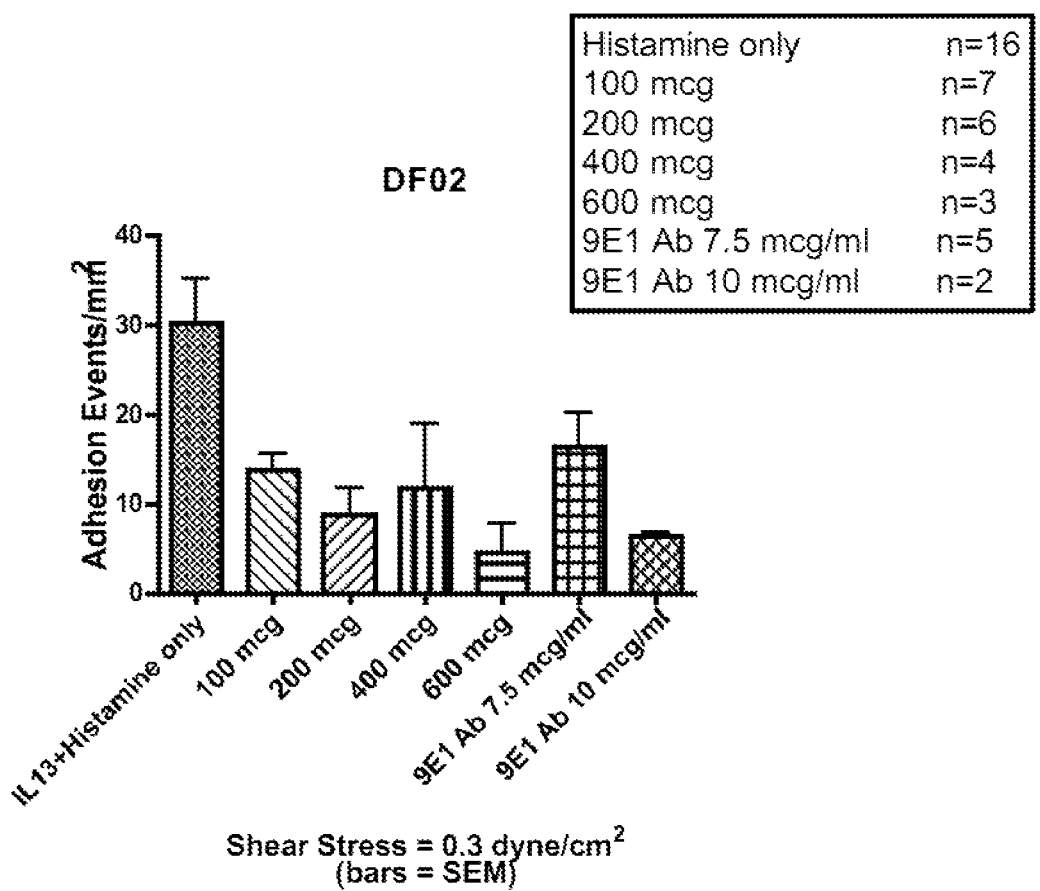
FIG. 5 demonstrates how a heparin derivative according to the invention is able to inhibit SS RBC adhesion to endothelial cells treated with IL-13 and histamine.

Overall, DF02 was able to inhibit SS RBC adhesion to endothelial cells treated with IL-13 and histamine, and this inhibition exhibited a modest dose-response relationship (FIG. 5). Adhesion to HUVECs stimulated with IL13 and histamine was greater than adhesion to similarly stimulated HUVECs pretreated with DF02 at 100, 200, 400 and 600 µg/ml (p=0.047, 0.031, 0.094, 0.065) respectively, using a paired t-test in which each patient sample was only compared to itself prior to DF02 treatment. In a similar analysis, 7.5 µg/ml of functional P-selectin blocking monoclonal antibody 9E10 also significantly reduced adhesion (p=0.038, FIG. 5).

Figure 6A:
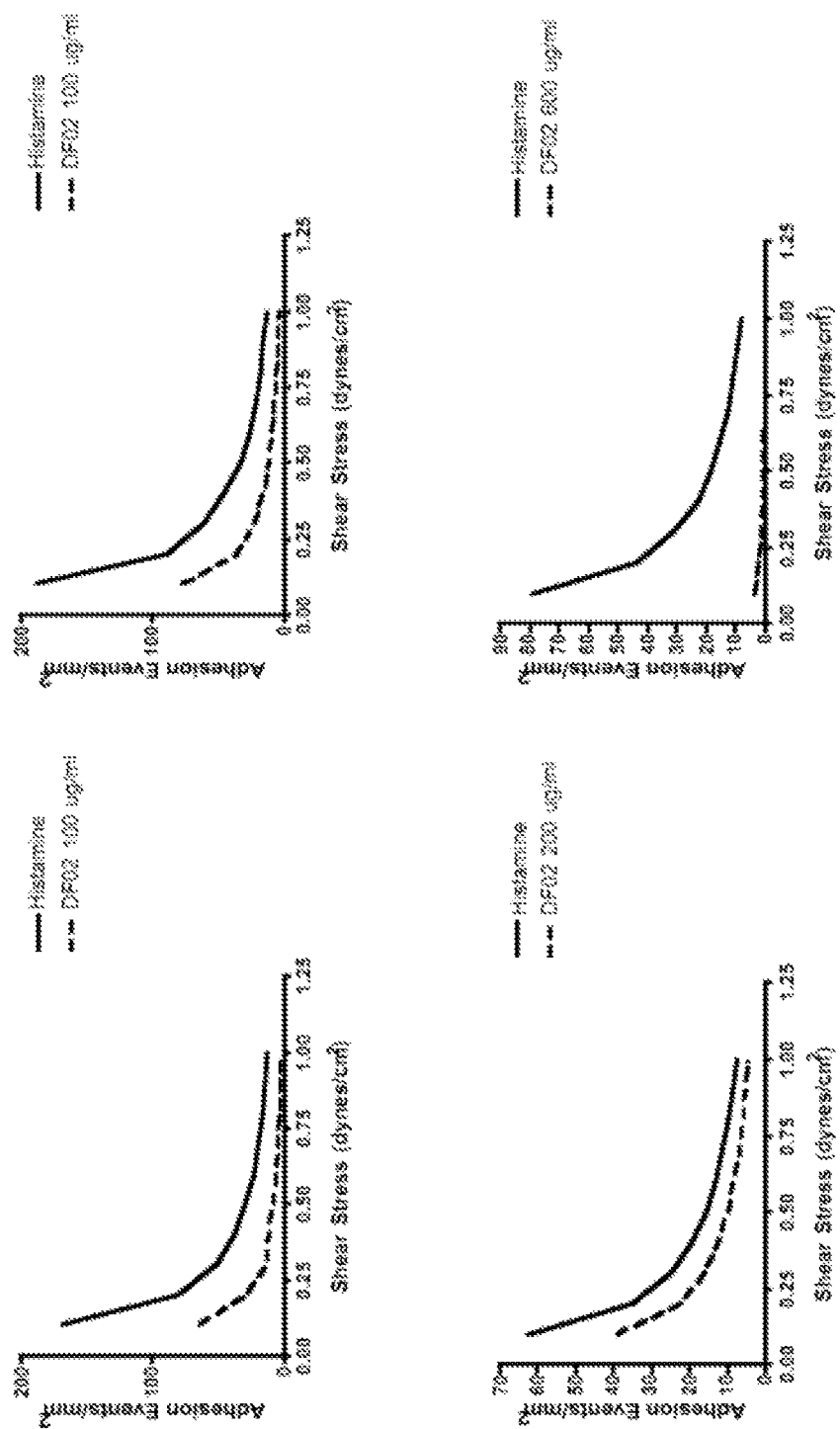
FIGS. 6A and 6B present sample graphs of adhesion events quantified at multiple shear stresses.
Figure 6B:
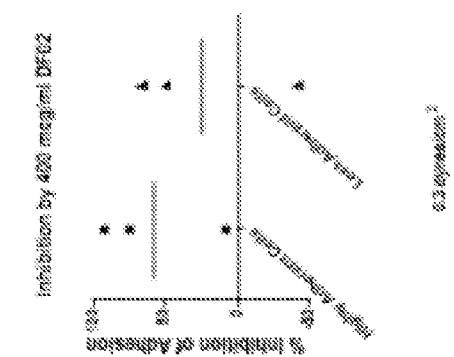
Figure 6B:
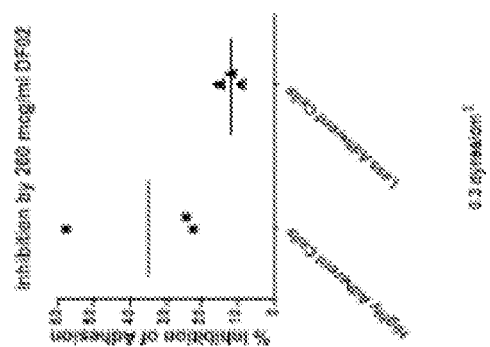
Figure 6B:
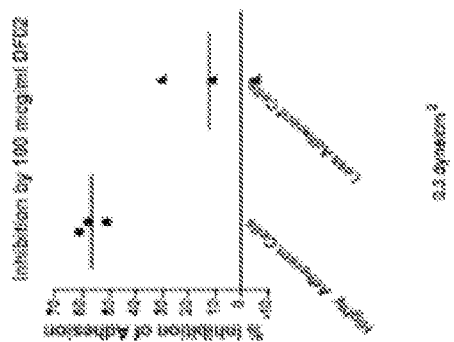

As illustrated in FIG. 6A, which presents sample graphs, adhesion events were quantified at multiple shear stresses. Because baseline adhesion of different patients' SS RBCs varied greatly, it is most valid to compare each patient's SS RBCs at different shear stress levels and pre and post treatment with DF02. Inhibition tended to be more pronounced with higher doses of DF02 and in patients with higher baseline adhesion (FIG. 6B). If divided into high and low adhesion groups there was a statistically significantly difference at the 100 µg/ml concentration of DF02 (p=0.02), with the high adhesion group responding better to treatment. In such analyses, 100 µg/ml DF02 also appeared to inhibit adhesion as much as did higher concentrations (FIG. 6B).

Figure 7:
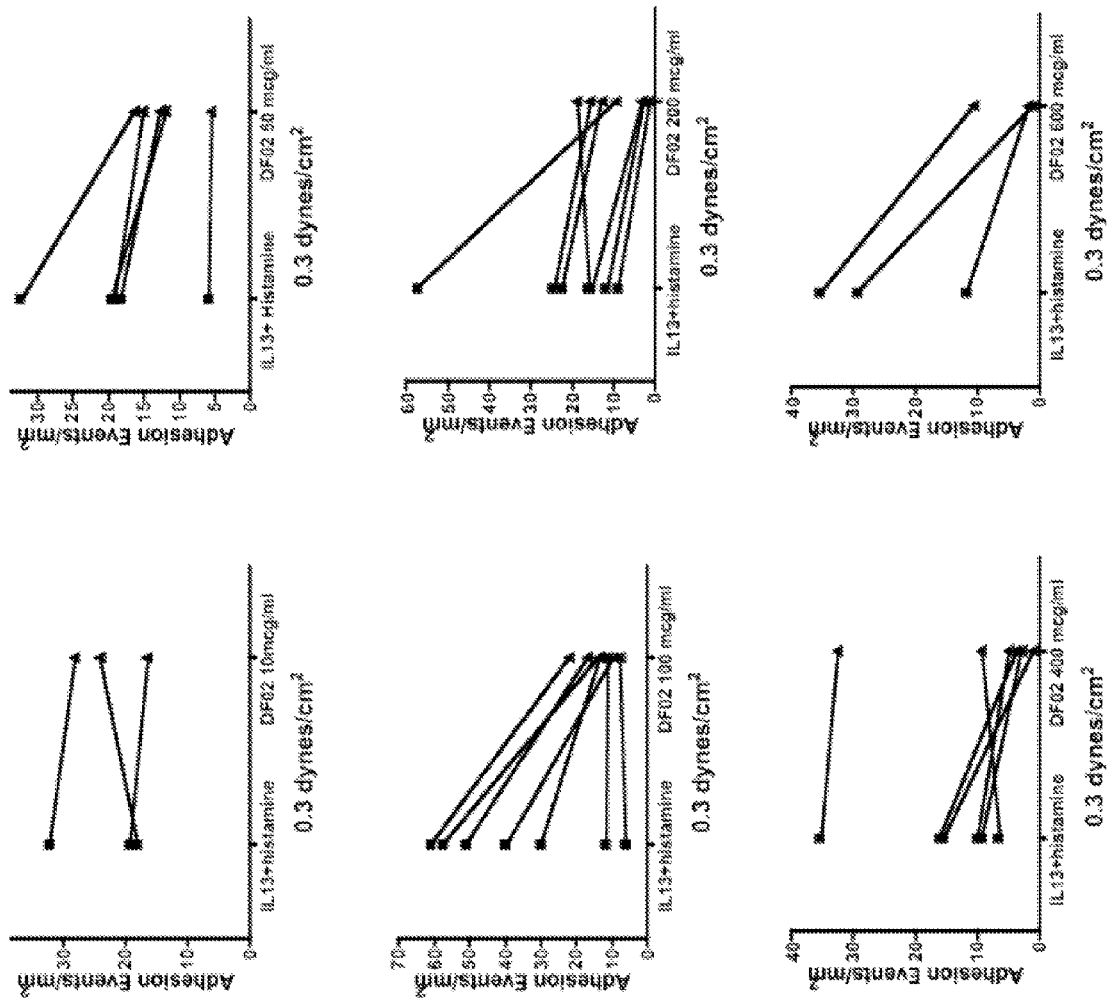
FIG. 7 demonstrates inhibition of adhesion events with DF02 treatment according to the present invention.

DF02 inhibited SS RBC adhesion as shown in detail in FIG. 7. Although there were fewer adhesive events at higher shear stresses, the effect of DF02 was similar (data not shown). However, little effect was observed when DF02 was used at 10 and 50 µg/ml, while the effect of 100 µg/ml was easily detectable.

Figure 8A:
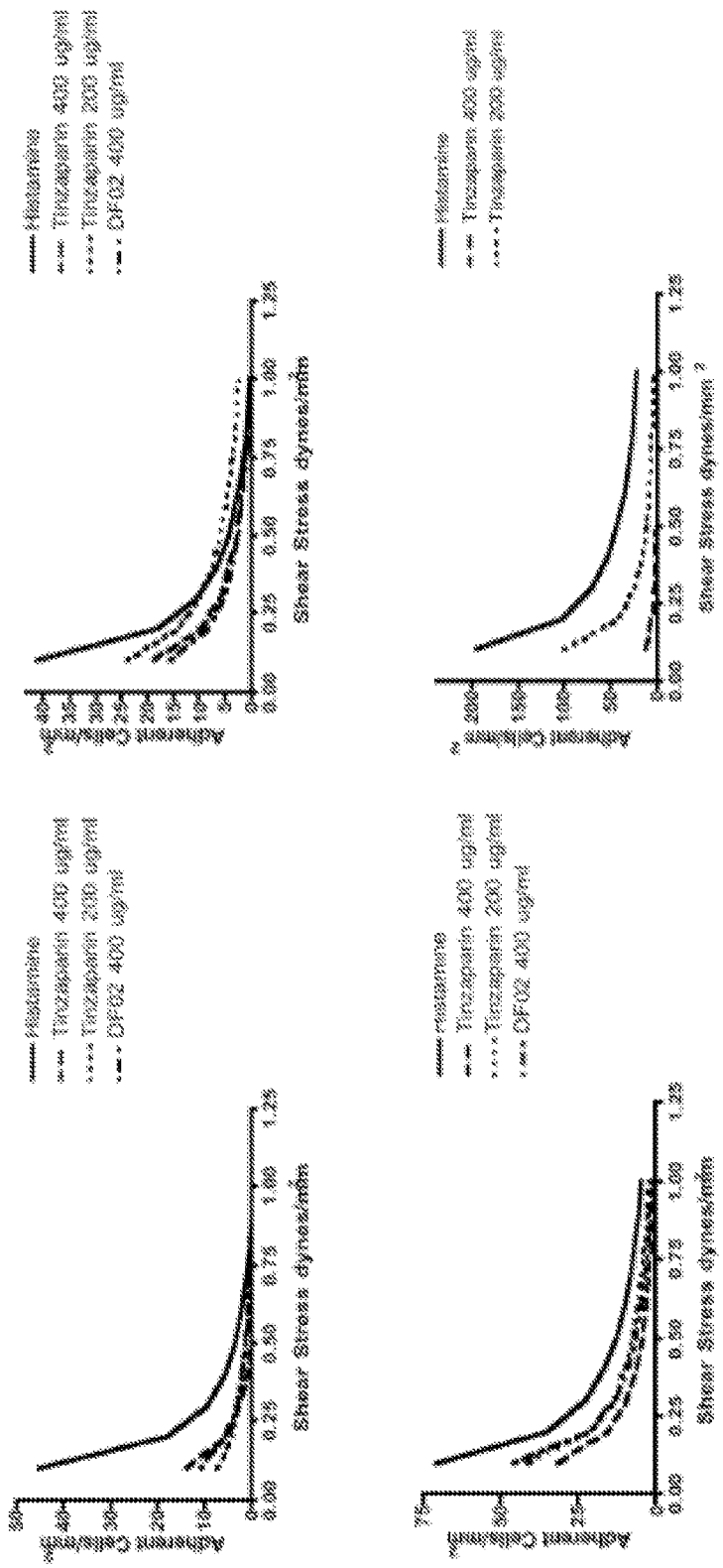
FIGS. 8A and 8B demonstrate comparison of inhibition of adhesion events with DF02 treatment according to the present invention, and the commercial LMWH tinzaparin.
Figure 8B:
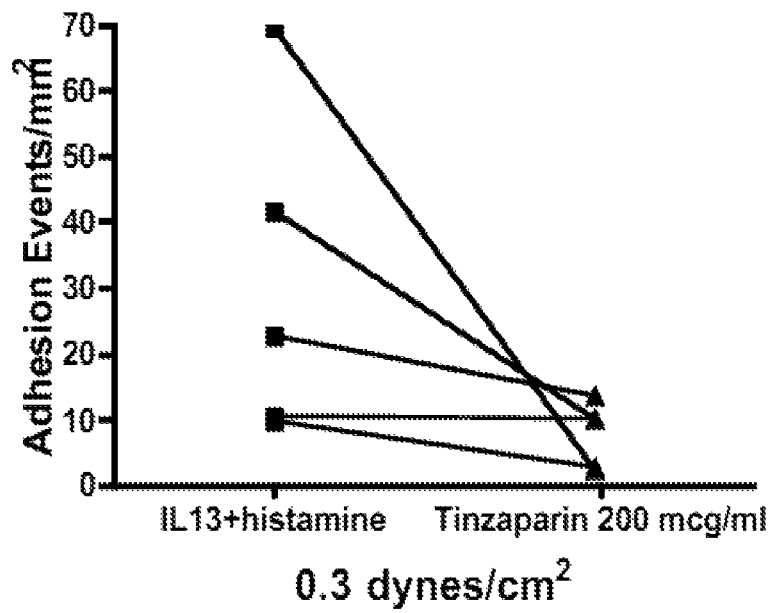
Figure 8B:
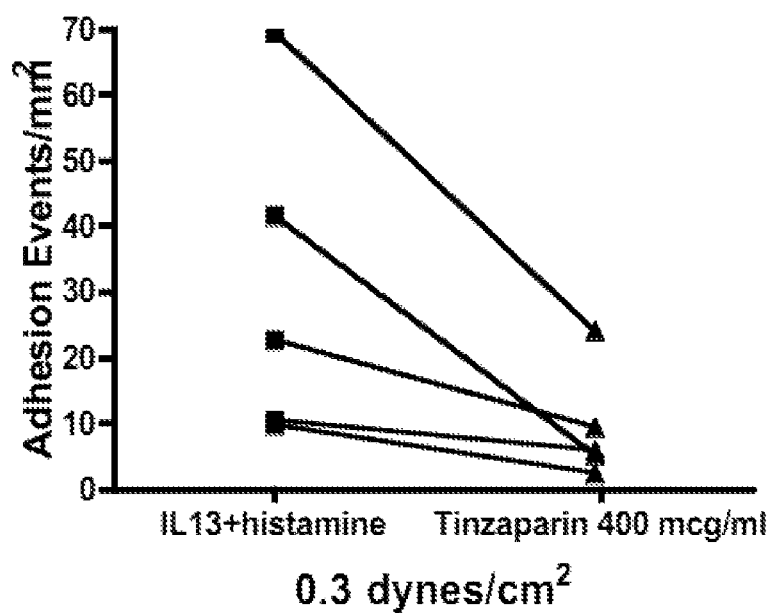

DF02 was also compared to tinzaparin for its ability to inhibit SS RBC adhesion to endothelial cells. Overall, tinzaparin was quite effective in reducing SS RBC adhesion. For most samples, DF02 at 400 µg/ml was equivalent to the same concentration of tinzaparin (see FIGS. 8A and B, with FIG. 7).

CONCLUSION

In summary, DF02 is active as an inhibitor of SS RBC adhesion to endothelial cells most probably via P-selectin. A source of variability could be the patients' cells, as their expression of ligands for various endothelial cell adhesion receptors, including P-selectin and αvβ3, could vary. In addition, the activation state of the erythroid adhesion receptors could vary among patients. Nevertheless, almost all patient samples showed less adhesion in the presence of DF02, and the degree of inhibition of adhesion was generally more pronounced with samples containing highly adherent cells. DF02 is an anti-adhesion agent useful in SCD, both to reduce RBC adhesion as well as potentially to reduce leukocyte adhesion, which has also been shown to be at least partly dependent on selectins.

EXAMPLE 7

In Vivo Functional Vaso-Occlusion Model

In order to verify the data in the previous presented in vitro examples, DF02 was evaluated using an animal model of sickle cell vaso-occlusion. The aim of the study was to investigate the activity of DF02 in blocking sickle red cell adhesion and sickle cell vaso-occlusion using in vivo assays of sickle red cell (SS RBC) adhesion to the endothelium, with and without infusion of DF02, or positive or negative control, in the window chamber nude mouse model of vaso-occlusion.

Method

These experiments utilize a previously described animal model (Zennadi et al. Blood 2007), in which window chambers are first implanted into the flanks of nude mice. Three to five days later, human normal or sickle red cells are infused into the mouse (usually through the tail vein) pre-treated with TNF-α (to induce inflammation and upregulate P-selectin expression); mice treated with vehicle only may be studied as controls. Female mice (nu-/nu-) 8-12 weeks in age from Jackson Laboratories, Bar Harbor, Me., were used to perform experiments described.

RBCs to be infused are pre-labelled with a fluorescent dye. The cells' adhesion may then be observed in subdermal blood vessels visible through the previously implanted window chambers. To determine the ability of DF02 to inhibit RBC adhesion, TNF-α-treated mice were infused with DF02 or control reagent prior to infusion of SS or normal RBCs. In addition, in some of these experiments, blood samples were drawn during the observation period in order to quantitate specific variables, such as cell survival. This model has the great advantages of providing direct visualization of cells in the context of whole blood and of allowing circulation of transfused cells under normal circulatory pressures. Furthermore, we have previously shown that human sickle red cells adhere to endothelium, induce leukocyte adhesion, and induce vaso-occlusion in this model system. Finally, we have shown that there is no detectable immune clearance of human red cells in these nu/nu mice.

Results

Studies of DF02 effect on vaso-occlusion was studied by injecting DF02 both before and after the induction of vaso-occlusion. In this model system, the occupancy of adhered SS-RBC can be quantified as well as the blood flow. The model shows inhibition and reversal of adhered SS-RBC by DF02 and a partial normalization of the blood flow.

Figure 9A:
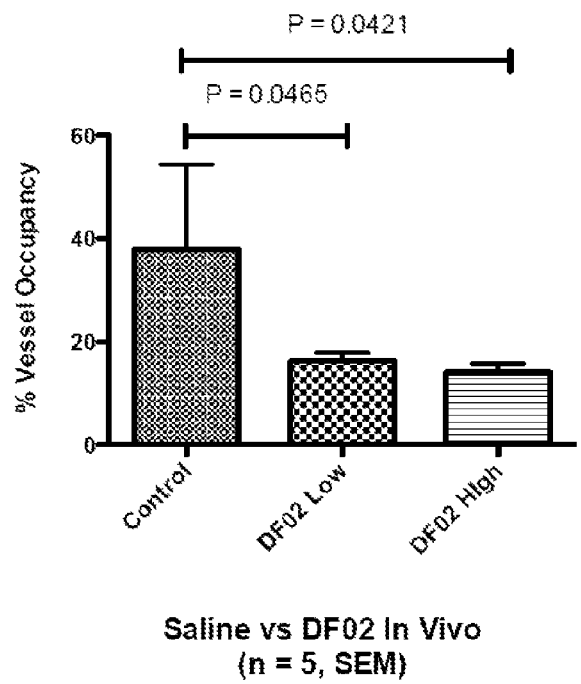
FIG. 9 present sample graphs of effect after treatment with DF02 according to the present invention, in comparison with the LMWH tinzaparin.

Vessel occupancy; a measure of the SS-RBC ability to bind to the blood vessel wall, was decreased by 50% by DF02 injection, as compared to a saline injection (FIG. 9A).

Figure 9B:
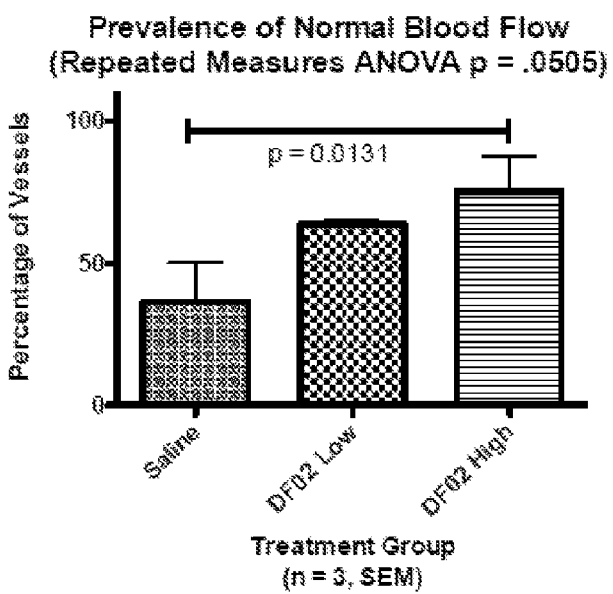

Furthermore, when quantifying the number of vessels that reached a normalized blood flow a dose dependent effect was detected when the animals were treated with DF02 (FIG. 9B).

The invention claimed is:

1. A method of treating sickle cell disease, comprising: administering to a patient having sickle cell disease a therapeutically effective amount of a chemically modified heparin having an antifactor IIa activity and an antifactor Xa activity, wherein the antifactor IIa activity is less than 10 IU/mg and the antifactor Xa activity is up to 10 IU/mg, the chemically modified heparin having a weight average molecular weight from about 6.5 to about 9.5 kDa, wherein the chemically modified heparin comprises polysaccharide chains having:

(i) at least 90% of the sulfate groups of the corresponding native heparin;

(ii) a reduction in chemically intact saccharide sequences providing an antithrombin-mediated anticoagulant effect, when compared to the polysaccharide chains of native heparin, and a reduction in unsulfated iduronic and/or glucuronic acid units when compared to native heparin; and (iii) a predominant disaccharide having the chemical structure:

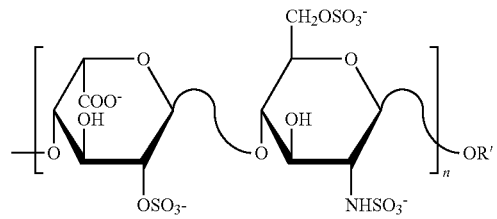

wherein R' is a threonate residue and n is an integer of from 2 to 25, such that it comprises from 2 to 25 disaccharide units corresponding to molecular weights from 1.2 to 15 kDa.

2. The method according to claim 1, wherein at least 30% of the polysaccharide chains have a molecular weight of at least 8 kDa.

3. The method according to claim 1, wherein the polysaccharide chains have glycol-split residues of the chemical structure:

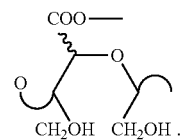

4. The method according to claim 1, wherein 3-15% of the polysaccharide chains have a molecular mass of at least 15 kDa.

5. The method according to claim 1, wherein from 25-47% of the polysaccharide chains have a molecular mass of at least 9 kDa.

6. The method according to claim 1, wherein from 40-60% of the polysaccharide chains have a molecular mass of at least 7 kDa.

7. The method according to claim 1, wherein from 60-80% of the polysaccharide chains have a molecular mass of at least 5 kDa.

8. The method according to claim 1, wherein at least 85% of the polysaccharide chains have a molecular mass of at least 3 kDa.

9. The method according to claim 1, wherein at least 95% of the polysaccharide chains have a molecular mass of at least 2 kDa.

10. The method according to having claim 1, wherein the chemically modified heparin has, in a $^1$H-NMR spectrum, no unidentified signals in the ranges 0.10-2.00 ppm, 2.10-3.10 ppm and 5.70-8.00 ppm larger than 4 percent when compared to the height of the signal present in native heparin at 5.42 ppm.

11. The method according to claim 1, wherein the predominantly occurring polysaccharide chains have from 6 to 16 disaccharide units with molecular weights from about 3.6 to about 9.6 kDa.

12. The method according to claim 1, the treatment is of vaso-occlusive crisis in sickle cell disease.

* * * * *